(12) United States Patent
Cedilote et al.

(10) Patent No.: US 7,838,693 B2
(45) Date of Patent: Nov. 23, 2010

(54) PROCESS FOR THE PREPARATION OF 3,5-DI-O-ACYL-2-FLUORO-2-C-METHYL-D-RIBONO-GAMMA-LACTONE

(75) Inventors: Miall Cedilote, Florence, SC (US);
Thomas Cleary, Florence, SC (US);
Hans Iding, Rheinfelden (DE);
Pingsheng Zhang, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 520 days.

(21) Appl. No.: 11/953,900

(22) Filed: Dec. 11, 2007

(65) Prior Publication Data
US 2008/0145901 A1 Jun. 19, 2008

Related U.S. Application Data

(60) Provisional application No. 60/875,617, filed on Dec. 18, 2006.

(51) Int. Cl.
*C07D 317/30* (2006.01)
*C07D 307/33* (2006.01)
*C12P 17/04* (2006.01)

(52) U.S. Cl. .................. 549/454; 549/318; 435/126
(58) Field of Classification Search ............... 549/318, 549/454; 435/126
See application file for complete search history.

(56) References Cited

U.S. PATENT DOCUMENTS

2005/0009737 A1  1/2005  Clark
2005/0025916 A1  2/2005  Nakanishi

FOREIGN PATENT DOCUMENTS

WO  WO2006/012440  2/2006

OTHER PUBLICATIONS

H. Ansel et al., Pharmaceutical Dosage Forms & Drug Delivery system (6th Ed. 1995) pp. 196-197.

*Primary Examiner*—Bernard Dentz
(74) *Attorney, Agent, or Firm*—George W. Johnston; Patricia S. Rocha-Tramaloni; Kimberly J. Prior

(57) ABSTRACT

The present invention provides novel methods for preparing a key intermediate, 3,5-di-O-acyl-2-fluoro-2-C-methyl-D-ribono-γ-lactone (2), for the preparation of 1-(2-deoxy-2-fluoro-2-C-methyl-β-D-ribofuranosyl)cytosine (1), which is a potent and selective anti-hepatitis C virus agent.

24 Claims, No Drawings

PROCESS FOR THE PREPARATION OF 3,5-DI-O-ACYL-2-FLUORO-2-C-METHYL-D-RIBONO-GAMMA-LACTONE

PRIORITY TO RELATED APPLICATIONS

This application claims the benefit of U.S. Provisional Application No. 60/875,617, filed Dec. 18, 2006, which is hereby incorporated by reference in its entirety.

FIELD OF THE INVENTION

The present invention provides novel methods for preparing a key intermediate, 3,5-di-O-acyl-2-fluoro-2-C-methyl-D-ribono-γ-lactone (2), for the preparation of 1-(2-deoxy-2-fluoro-2-C-methyl-β-D-ribofuranosyl)cytosine (1), which is a potent and selective anti-hepatitis C virus agent.

BACKGROUND OF THE INVENTION

Hepatitis C virus (HCV) infection is a major health concern that leads to chronic liver disease in a substantial number of patients. This viral disease is transmitted sexually and parenterally by contaminated blood, blood products, and contaminated needles. Current treatments for HCV infection are limited to immunotherapy with interferon-α, either alone, or in combination with ribavirin [1-(β-D-ribofuranosyl)-1H-1,2,4-triazole-3-carboxamide).

The HCV virion is a small, enveloped positive-strand RNA virus in the Flaviviridae family. The genome contains a single open reading frame encoding a polyprotein of over 3,000 amino acids, which is cleaved to generate the mature structural and non-structural viral proteins. The single open reading frame is flanked by 5' and 3' non-translated regions of a few hundred nucleotides in length, which are important for RNA translation and replication. The translated polyprotein contains the structural core and envelope proteins (E1, E2, p7) at the N-terminus, followed by the nonstructural proteins (NS2, NS3, NS4A, NS4B, NS5A, and NS5B). The mature structural proteins are generated via cleavage by the host signal peptidase. The junction between NS2 and NS3 is autocatalytically cleaved by the NS2/NS3 protease, while the remaining four junctions are cleaved by the N-terminal serine protease domain of NS3 complexed with NS4A. The NS3 protein also contains the NTP-dependent helicase activity, which unwinds duplex RNA during replication. The NS5B protein possesses RNA-dependent RNA polymerase activity, which is essential for viral replication. Unlike Hepatitis B virus (HBV) or Human Immunodeficiency Virus (HIV), no DNA is involved in the replication of HCV.

United States published patent application no. 2005-0009737 discloses that 1-(2-deoxy-2-fluoro-2-C-methyl-β-D-ribofuranosyl)cytosine (1) is a potent and selective anti-HCV agent. The synthetic procedures for preparing compound 1 are inefficient with overall yields at or below 4%.

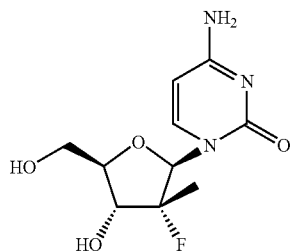

1

A key intermediate for preparing compound 1 is 3,5-di-O-acyl-2-fluoro-2-C-methyl-D-ribono-γ-lactone (2).

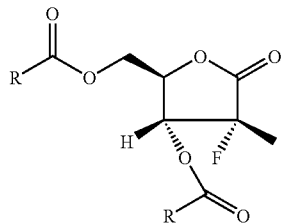

2

A number of synthetic routes for preparing intermediate 2 have been disclosed in PCT/US2005/025916, but these synthetic routes have the shortcomings of high manufacturing costs and technical difficulties for commercial scale manufacturing. The use of heavy load of asymmetric dihydroxylation catalyst (AD-mix-β), fluorinating agent diethylaminosulfur trifluoride, and the Wittig reagent, etc., are the major cost drivers. The use of highly toxic reagents, such as AD-mix-β, highly reactive reagent such as diethylaminosulfur trifluoride, and chromatographic isolation of intermediates, etc. contribute to scale up difficulties.

Accordingly, a novel and cost effective method for the preparation of intermediate 2 is required.

SUMMARY OF THE INVENTION

The present invention provides a method for preparing a mixture of compounds of the formula 22, 23, and 24:

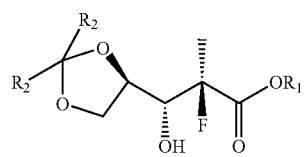

22

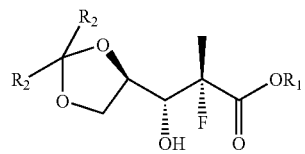

23

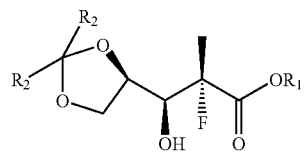

24 which comprises:
(a) reacting a compound of the formula 20

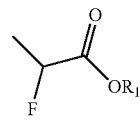

20 with a non-nucleophilic base-I in a non-reactive solvent; and (b) reacting the mixture from step (a) with a compound of the formula 21;

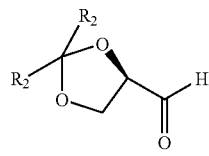
21 to provide compounds 22, 23, and 24, wherein $R_1$ is a straight chain $C_1$-$C_4$ alkyl group and $R_2$ is selected from the group consisting of methyl, ethyl, n-propyl and n-butyl.

The present invention also provides a method for preparing a mixture of compounds of the formula 22 and 24:

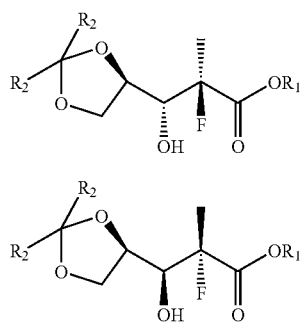
22

24 which comprises:

(a) reacting a mixture of compounds of the formula 22, 23, and 24:

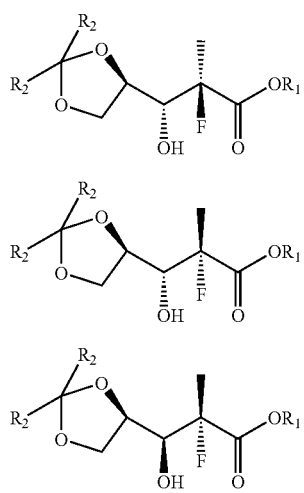
22

23

24 with an enzyme which preferentially hydrolyzes compound 23 to the corresponding carboxylic acid in an alkaline aqueous medium; and (b) extracting the alkaline aqueous medium from step (a) with a volatile organic solvent to provide compounds 22 and 24;

wherein $R_1$ is a straight chain $C_1$-$C_4$ alkyl group and $R_2$ is selected from the group consisting of methyl, ethyl, n-propyl and n-butyl.

The present invention further provides a method for preparing a compound of the formula 2:

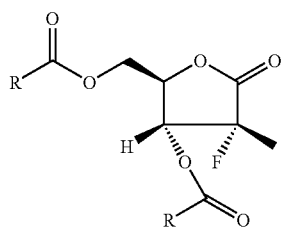
2 which comprises:

(a) acidically hydrolyzing a mixture of compounds of the formula 22 and 24:

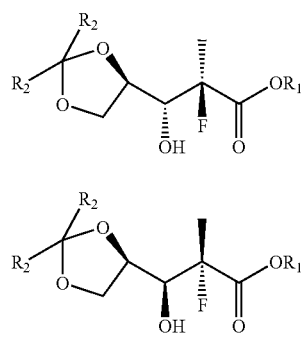
22

24 to form a mixture of compounds of the formula 25 and 26:

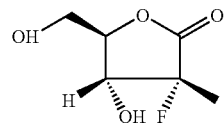
25

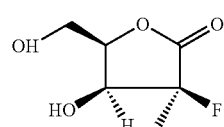
26

(b) acylating compounds 25 and 26 from step (a) with an acyl halide, RCOX, or an acyl anhydride, RC(O)O(O)CR, in the presence of a non-nucleophilic base-II, which does not react with acyl halides, in a non-reactive solvent to form compounds of the formula 2 and 27; and

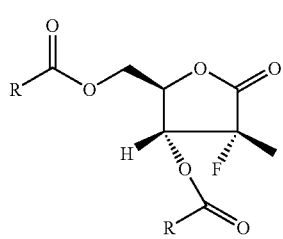
2

-continued

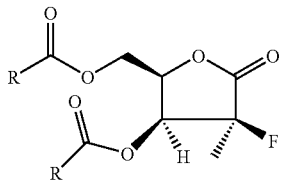
27

(c) recrystallizing the mixture of compounds 2 and 27 from step (b) from an aqueous-soluble organic solvent capable of providing crystalline compound 2; wherein R is a straight or branched $C_1$-$C_6$ alkyl group or is an arylalkyl group substituted with one or two $C_1$-$C_3$ alkyl groups; $R_1$ is a straight chain $C_1$-$C_4$ alkyl group; $R_2$ is selected from the group consisting of methyl, ethyl, n-propyl and n-butyl; and X is halogen.

The present invention still further provides a method for preparing a compound of the formula 22:

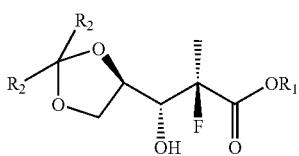
22 which comprises:

(a) providing a mixture of compounds of the formula 22 and 24:

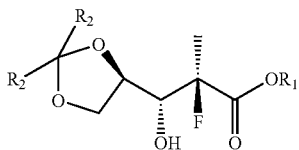
22

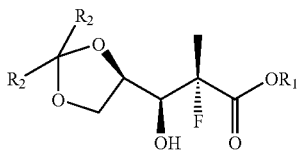
24

(b) recrystallizing the mixture of compounds 22 and 24 from step (a) from a volatile organic solvent to provide compound 22;

wherein $R_1$ is a straight chain $C_1$-$C_4$ alkyl group and $R_2$ is selected from the group consisting of methyl, ethyl, n-propyl and n-butyl.

The present invention yet further provides novel compounds of the formulae 22, 23, 24, and 26.

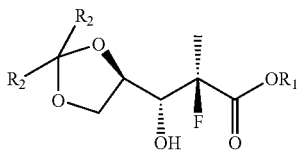
22

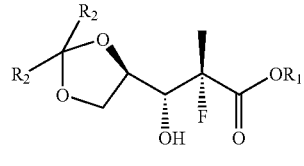
23

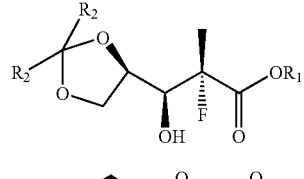
24

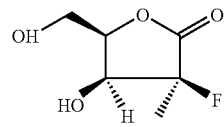
26 wherein $R_1$ is a straight chain $C_1$-$C_4$ alkyl group and $R_2$ is selected from the group consisting of methyl, ethyl, n-propyl and n-butyl.

DETAILED DESCRIPTION OF THE INVENTION

The present invention provides new methods for preparing a key intermediate, 3,5-di-O-acyl-2-fluoro-2-C-methyl-D-ribono-γ-lactone (2), for the preparation of 1-(2-deoxy-2-fluoro-2-C-methyl-β-D-ribofuranosyl)cytosine, which is a potent and selective anti-hepatitis C virus agent. The advantages of this new method include 1) the use of less toxic and less expensive materials; 2) fewer chemical transformations; and 3) only one purification (recrystallization) step to obtain the pure product. The new method results in a much more cost effective and operable manufacturing process As used herein, the following terms have the given meanings:

The term "arylalkyl", as used herein refers to an aryl group with an alkyl substituent, as for example, benzyl.

The term "catalytic amount", as used herein, refers to that amount of catalyst necessary to promote a chemical reaction. Although a catalyst undergoes no chemical change, it is often physically altered by the chemical reactants. The exact amount of catalyst necessary to promote a chemical reaction varies by the type of catalyst as well as the reactants employed and is readily determined by one skilled in the art.

The term "diastereomerically enriched" refers to a composition that comprises at least about 90%, and preferably about 95%, 98%, 99% or 100% of a single diastereomer of that composition.

The term "halogen" refers to chloro, bromo, iodo and fluoro, and is preferably chloro.

The term "non-reactive solvent" refers to a solvent that does not chemically interfere with the reaction.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hygroscopicity, and solubility of compounds. See, e.g., H. Ansel et. al., Pharmaceutical Dosage Forms and Drug Delivery Systems (6$^{th}$ Ed. 1995) at pp. 196 and 1456-1457.

The term "preferentially hydrolyzes" refers to an enzyme that selectively hydrolyzes a diastereomer (a compound that has more than one chiral center) in a mixture of diastereomers, to provide a mixture diastereomerically enriched in the non-hydrolyzed diastereomers.

The term "prodrug" refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "protecting group" refers to a group that is added to an oxygen or nitrogen atom to prevent its further reaction. A wide variety of oxygen and nitrogen protecting groups are known to those skilled in the art of organic synthesis. Common protecting groups are disclosed in T. W. Greene and P. G. M. Wuts, "Protective groups in Organic Synthesis," 3rd ed., John Wiley& Sons, 1999, which disclosure is incorporated herein by reference.

The term "volatile organic solvent" refers to a water-insoluble organic solvent having a boiling point below 130° C., preferably below 110° C., and more preferably below 100° C. Non-limiting examples of volatile organic solvents include methylene chloride, chloroform, carbon tetrachloride, diethyl ether, hexane, and the like.

The present invention provides a novel synthesis of key intermediate 3,5-di-O-acyl-2-fluoro-2-C-methyl-D-ribono-γ-lactone (2) for the preparation of 1-(2-deoxy-2-fluoro-2-C-methyl-β-D-ribofuranosyl)cytosine (1), which is a potent and selective anti-hepatitis C virus agent. A preferred novel synthesis of 2 is set out below.

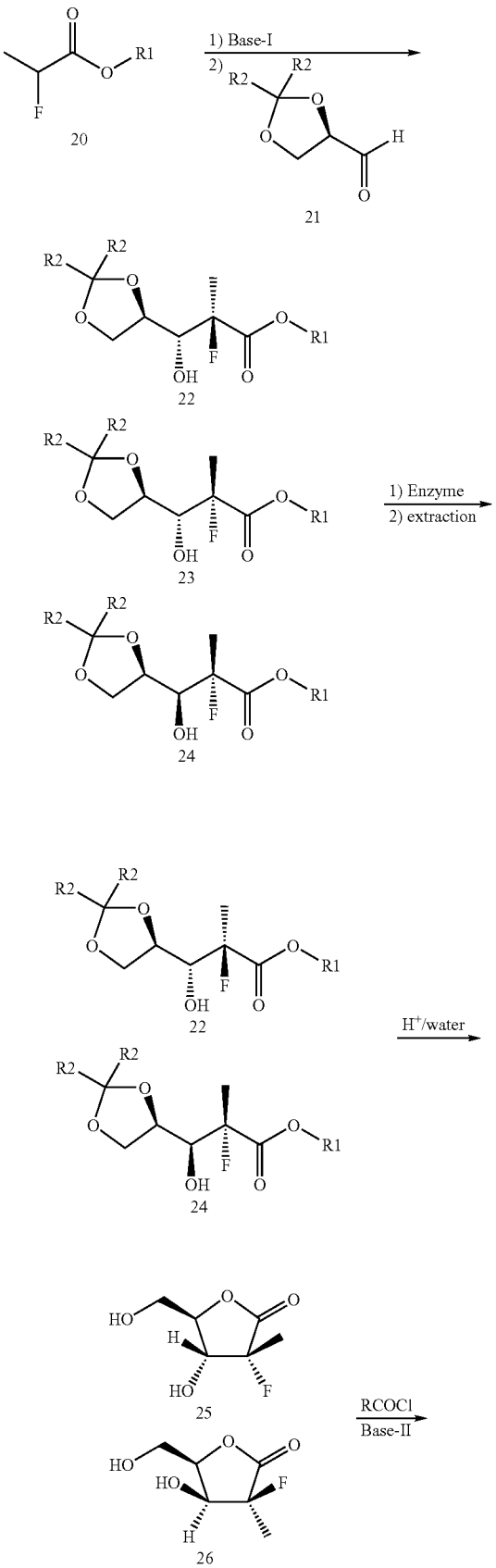

-continued

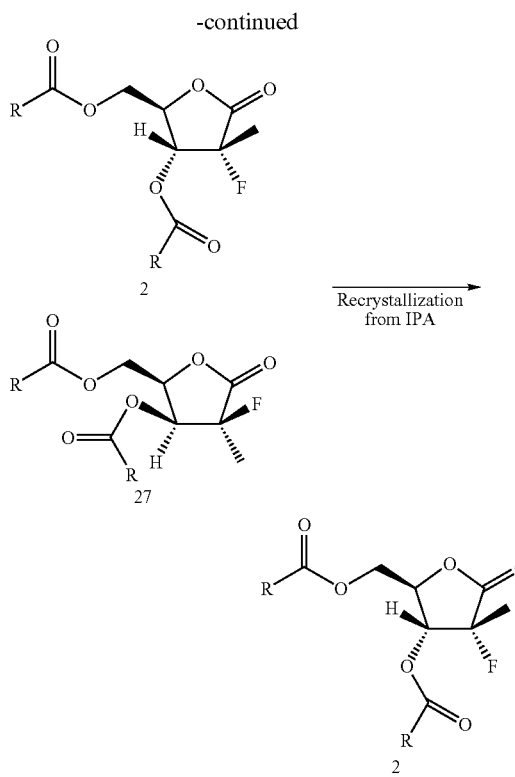

In this scheme, an aldol condensation between an enolate of 2-fluoropropionate (20) is generated via the reaction of 20 and base-I, and a protected D-glyceraldehyde (21). The reaction produces a mixture of three isomeric products, 22, 23, and 24, with the desired product, 22, as the major isomer. The mixture is then treated with an enzyme, which preferentially hydrolyzes the major by-product (23) to the corresponding acid, which is then removed during an extractive workup. The resulting mixture of 22 and 24 is then treated with an acid in aqueous solution to form a mixture of 25 and 26. A subsequent acylation using an acyl chloride or an anhydride and a non-nucleophilic base-II, which does not react with acyl halides, produces a mixture of 2 and 27. Recrystallization of the mixture from a suitable solvent affords pure 2.

In a specific embodiment, the present invention provides a method for preparing a mixture of compounds of the formula 22, 23, and 24:

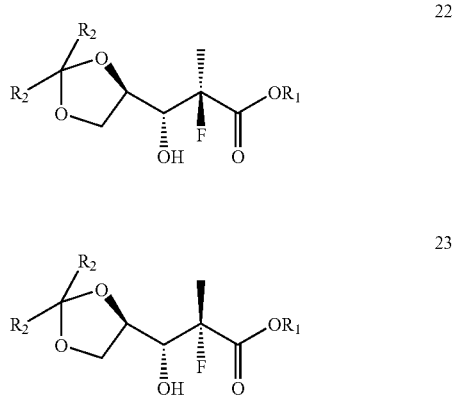

-continued

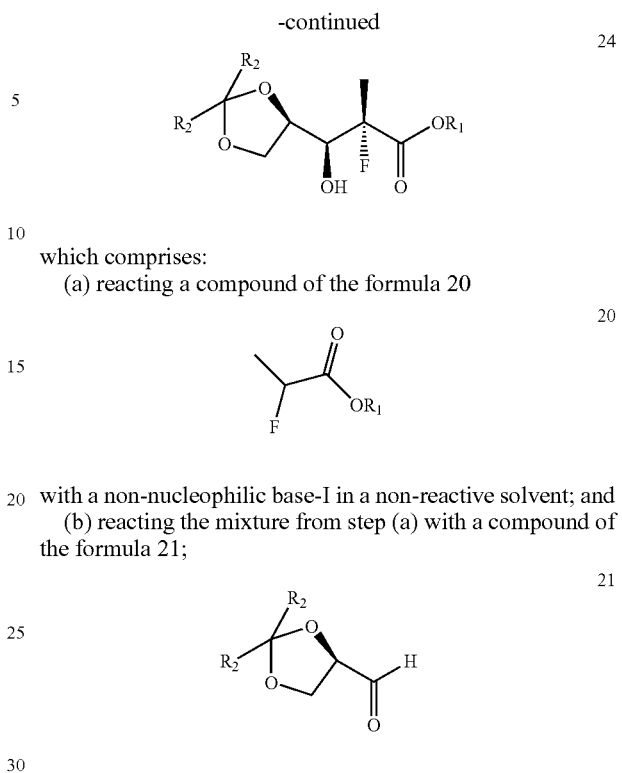

which comprises:
(a) reacting a compound of the formula 20 with a non-nucleophilic base-I in a non-reactive solvent; and
(b) reacting the mixture from step (a) with a compound of the formula 21;

to provide compounds 22, 23, and 24, wherein $R_1$ is a straight chain $C_1$-$C_4$ alkyl group and $R_2$ is selected from the group consisting of methyl, ethyl, n-propyl and n-butyl.

In this embodiment, $R_1$ is a straight chain $C_1$-$C_4$ alkyl group, preferably $R_1$ is methyl or ethyl, and more preferably $R_1$ is ethyl. $R_2$ is selected from the group consisting of methyl, ethyl, n-propyl and n-butyl, preferably $R_2$ is methyl or ethyl, and more preferably $R_2$ is methyl.

In step (a), any strong non-nucleophilic base may be used as base-I. Non-limiting illustrative examples include lithium diisopropylamide (LDA), lithium 2,2,6,6-tetramethylpiperdine (LTMP), lithium hexamethyldisilazide (LHMDS), and the like.

In step (a), the reaction can be carried out in a non-reactive solvent, that is, a solvent that does not chemically interfere with the reaction. Non-limiting illustrative examples include tetrahydrofuran (THF), 2-Me-THF, toluene, diethyl ether, tert-butyl methyl ether, and the like.

In another specific embodiment, the present invention provides a method for preparing a mixture of compounds of the formula 22 and 24:

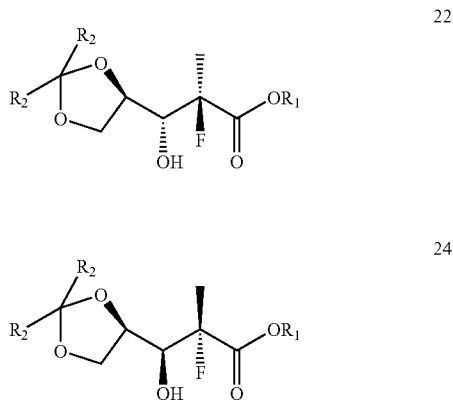

which comprises:

(a) reacting a mixture of compounds of the formula 22, 23, and 24:

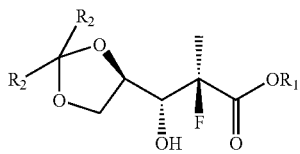
22

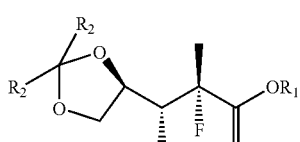
23

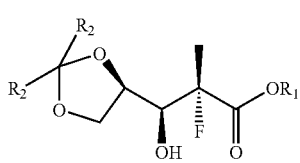
24 with an enzyme which preferentially hydrolyzes compound 23 to the corresponding carboxylic acid in an alkaline aqueous medium; and (b) extracting the alkaline aqueous medium from step (a) with a volatile organic solvent to provide compounds 22 and 24;

wherein $R_1$ is a straight chain $C_1$-$C_4$ alkyl group and $R_2$ is selected from the group consisting of methyl, ethyl, n-propyl and n-butyl.

In this embodiment, $R_1$ and $R_2$ are as described above.

In step (a), any enzyme may be employed which preferentially hydrolyzes compound 23 to the corresponding carboxylic acid in the presence of compounds 22 and 24. *Candida Antarctica* lipase form B (CALB), Novozymes, is a preferred enzyme because of its high reactivity and stereoselectivity. Preferably, the selective hydrolysis of compound 23 is carried out with CALB at a temperature of about 20-45° C. in an aqueous buffer of about pH 7.0-7.5 that may contain ammonium sulfate, potassium sulfate, sodium sulfate, dimethylammonium phosphate, sodium acetate, sodium citrate, sodium phosphate, sorbitol, sucrose, glycine or other beneficial additives for the enzymatic activity.

Other useful enzymes in step (a), which preferentially hydrolyze compound 23 in the presence of compound 22, include the lipase TOY from *Pseudomonas aeruginosa* (Toyobo); the esterase HLE from horse liver (Fluka), the esterase MME from *Mucor miehei* (Fluka); the esterase CLE from *Candida lipolytica* (Fluka); the lipase L1 from *Burholderia cepacia* (Roche); and the purified formulation of CALB which is the of lipase L2 from Roche. The additional presence of compound 24 in the mixture of compounds of the formula 22, 23, and 24 might be hydrolyzed, partially hydrolyzed or remain as an ester during the enzymatic hydrolysis. This will not influence the usefulness of the enzymes.

In step (b), the extraction of the mixture of compounds 22 and 24 from the alkaline aqueous medium may be carried out with any conventional volatile organic solvent, preferably dichloromethane.

In another specific embodiment, the present invention provides a method for preparing a compound of the formula 2:

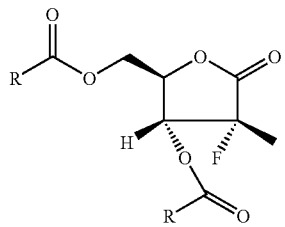
2 which comprises:

(a) acidically hydrolyzing a mixture of compounds of the formula 22 and 24:

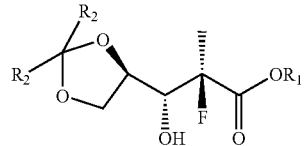
22

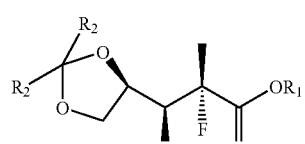
24 to form a mixture of compounds of the formula 25 and 26:

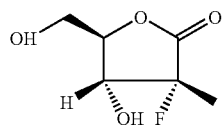
25

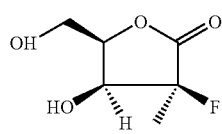
26

(b) acylating compounds 25 and 26 from step (a) with an acyl halide, RCOX, or an acyl anhydride, RC(O)O(O)CR, in the presence of a non-nucleophilic base-II, which does not react with acyl halides, in a non-reactive solvent to form compounds of the formula 2 and 27; and

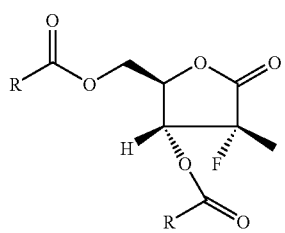
2

-continued

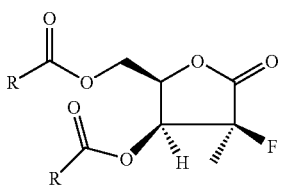

(c) recrystallizing the mixture of compounds 2 and 27 from step (b) from an aqueous-soluble organic solvent capable of providing crystalline compound 2; wherein R is a straight or branched $C_1$-$C_6$ alkyl group or is an arylalkyl group substituted with one or two $C_1$-$C_3$ alkyl groups; $R_1$ is a straight chain $C_1$-$C_4$ alkyl group; $R_2$ is selected from the group consisting of methyl, ethyl, n-propyl and n-butyl; and X is halogen.

In this embodiment, $R_1$ and $R_2$ are as described above. R is a straight or branched $C_1$-$C_6$ alkyl group or is an arylalkyl group substituted with one or two $C_1$-$C_3$ alkyl groups. Preferably, R is a straight or branched $C_1$-$C_3$ alkyl group or a phenyl group, more preferably R is phenyl.

In step (a), non-limiting illustrative examples of acids that may be used in the acidic hydrolyzing may be selected from the group consisting of acetic acid, sulfuric acid, hydrochloric acid, methanesulfonic acid, trifluoroacetic acid, and the like. Conversion of 22 and 24 to the corresponding 25 and 26 in step (a) may be carried out using an acid as catalyst in a mixed solution of an organic solvent and water at an elevated temperature. Suitable conditions include acetic acid/water/95° C.; Amberlyst 15/acetonitrile/water/82° C.; sulfuric acid/ethanol/water/80° C.; and hydrochloric acid/1-propanol/water/88° C.

In step (b), acylation of compounds 25 and 26 may be performed using an acyl halide, RCOX, or an acyl anhydride, RC(O)O(O)CR, wherein R is defined above, and a non-nucleophilic base-II, which does not react with acyl halides. X is halogen. A preferred acyl halide is benzoyl chloride.

In step (b), any non-nucleophilic base may be used as base-II, which does not react with acyl halides. Non-limiting illustrative examples of base-II include pyridine, triethylamine, N,N'-diisopropylamine (DIPEA), 4-dimethylaminopyridine (DMAP), and other tertiary amines. The non-nucleophilic base-II is preferably a tertiary amine.

In step (b), non-limiting illustrative examples of solvents that may be used include acetonitrile, dimethylformamide (DMF), pyridine, and the like.

In step (c), the aqueous-soluble organic solvent employed may be any solvent that substantially separates compound 2 in the crystalline form from compound 27. Non-limiting illustrative examples may be selected from the group consisting of methanol, ethanol, n-propanol, and isopropanol. A preferred solvent is isopropanol.

In another specific embodiment, the present invention provides a method for preparing a compound of the formula 22:

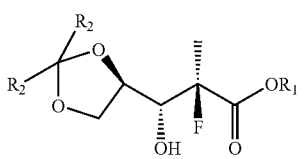

which comprises:

(a) providing a mixture of compounds of the formula 22 and 24:

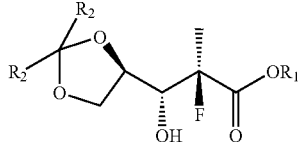

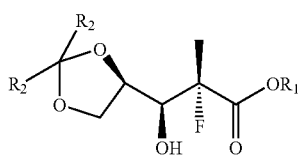

(b) recrystallizing the mixture of compounds 22 and 24 from step (a) from a volatile organic solvent to provide compound 22;

wherein $R_1$ is a straight chain $C_1$-$C_4$ alkyl group and $R_2$ is selected from the group consisting of methyl, ethyl, n-propyl and n-butyl.

In this embodiment, $R_1$ and $R_2$ are as described above.

In step (b), the solvent may be a $C_5$-$C_8$ hydrocarbon solvent, and more preferably is hexane. The method may further comprise dissolving compounds 22 and 24 in tert-butyl methyl ether and then adding hexane.

The present invention also provides novel compounds of the formulae 22, 23, 24, and 26:

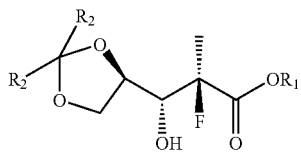

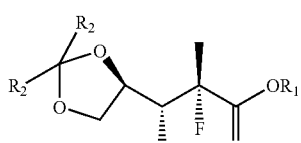

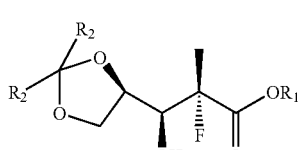

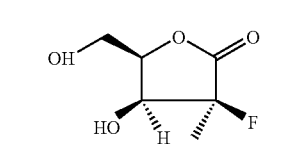

wherein $R_1$ and $R_2$ are straight or branched $C_1$-$C_6$ alkyl groups.

The compounds of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate key intermediates for the preparation of 1-(2-deoxy-2-fluoro-2-C-methyl-β-D-ribofuranosyl)cytosine (1).

Example 1

Reaction of ethyl 2-fluoropropionate (20, $R_1$=ethyl) with D-glyceraldehyde, 1,2-acetonide (21, $R_2$=methyl)

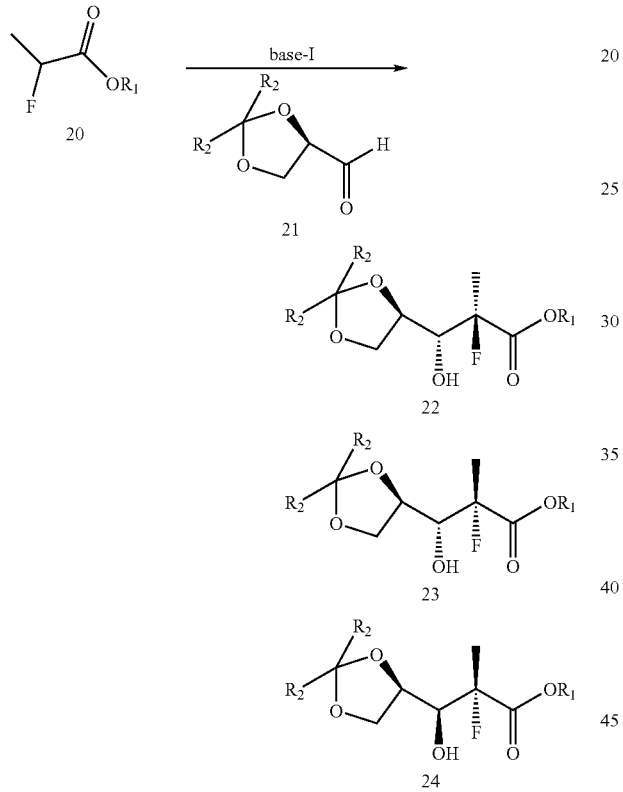

A dry, clean, 2 L, 4-neck round bottom flask, equipped with a mechanic stirrer, a thermo couple, a nitrogen inlet, and an addition funnel, was charged with 266 g of anhydrous tetrahydrofuran (THF) and 38.1 g of diisopropylamine. The mixture was stirred and cooled to <−75° C. To the solution was slowly charged 173 g of 1.6 M MeLi solution in ethyl ether while maintaining the batch temperature below −55° C. After the addition the mixture was stirred at approximately −75° C. for 40 minutes. To this mixture was then slowly added 45.2 g of ethyl 2-fluoropropionate 20 while maintaining the batch temperature below −74° C. The mixture was stirred at −76° C. for 50 minutes and a solution of 35 g freshly distilled D-glyceraldehyde, 1,2-acetonide 21 in 178 g of anhydrous THF was slowly added while maintaining batch temperature below −74° C. After the addition the mixture was stirred for approximately 20 minutes. To it was added 300 g of 20% $NH_4Cl$ solution. The mixture was slowly warmed to ambient temperature and transferred to a separatory funnel. The aqueous phase was separated and extracted with 2×132 g=264 g of dichloromethane. The organic phases were combined, dried over $MgSO_4$, filtered, and concentrated to give 58 g crude aldol product as a thick oil. A gas chromatogram showed the oil contained 12.2% of 24, 43.4% of 22, and 35.2% of 23.

Example 2

Reaction of ethyl 2-fluoropropionate (20, $R_1$=ethyl) with D-glyceraldehyde, 1,2-pentanonide (21, $R_2$=ethyl)

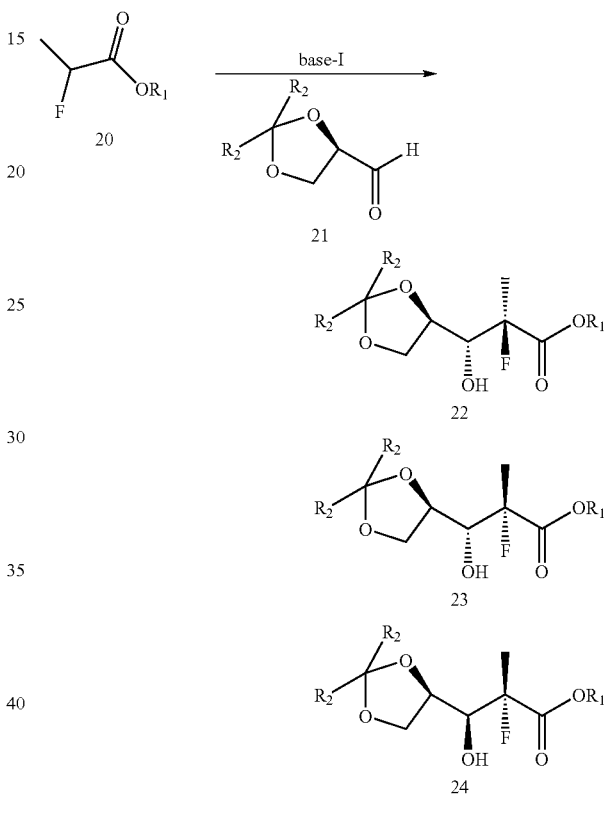

A dry, clean, 4-neck round bottom flask, equipped with a mechanic stirrer, a thermo couple, a nitrogen inlet, and an addition funnel, was charged with 20 mL of anhydrous THF and 1.8 g of diisopropylamine. The mixture was stirred and cooled to <−75° C. To the solution was slowly charged 11 mL of 1.6 M MeLi solution in ethyl ether while maintaining the batch temperature below −55° C. After the addition the mixture was stirred at approximately −75° C. for 30 minutes. To this mixture was then slowly added 2.1 g of ethyl 2-fluoropropionate 20 while maintaining the batch temperature below −74° C. The mixture was stirred at −76° C. for 30 minutes and a solution of 2 g freshly distilled D-glyceraldehyde, 1,2-pentanonide 21 in 10 mL of anhydrous THF was slowly added while maintaining batch temperature below −74° C. After the addition the mixture was stirred for approximately 20 minutes. To it was added 20 mL of 20% $NH_4Cl$ solution. The mixture was slowly warmed to ambient temperature and transferred to a separatory funnel. The aqueous phase was separated and extracted with 2×10 mL=20 mL of dichloromethane. The organic phases were combined, dried over $MgSO_4$, filtered, and concentrated to give 3 g crude aldol product as a thick oil. A gas chromatogram showed the oil contained 8.2% of 24, 36.5% of 22, and 30.8% of 23.

Example 3

Reaction of n-butyl 2-fluoropropionate (20, $R_1$=n-butyl) with D-glyceraldehyde, 1,2-acetonide (21, $R_2$=methyl)

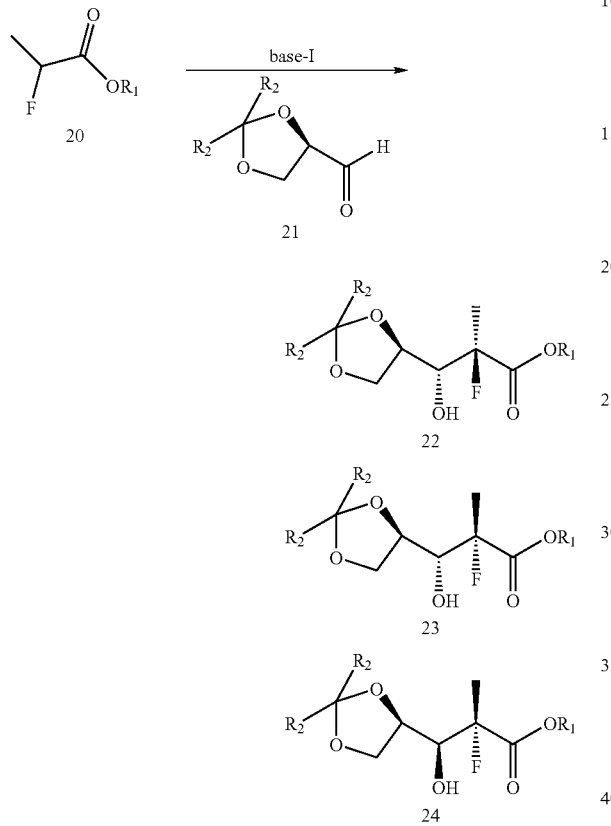

A dry, clean, 4-neck round bottom flask, equipped with a mechanic stirrer, a thermo couple, a nitrogen inlet, and an addition funnel, was charged with 100 mL of anhydrous toluene and 10 g of diisopropylamine. The mixture was stirred and cooled to <−75° C. To the solution was slowly charged 54 mL of 1.6 M MeLi solution in ethyl ether while maintaining the batch temperature below −55° C. After the addition the mixture was stirred at approximately −75° C. for 30 minutes. To this mixture was then slowly added 11 g of n-butyl 2-fluoropropionate 20 while maintaining the batch temperature below −70° C. The mixture was stirred at −76° C. for 30 minutes and a solution of 8 g freshly distilled D-glyceraldehyde, 1,2-acetonide 21 in 50 mL of anhydrous toluene was slowly added while maintaining batch temperature below −74° C. After the addition the mixture was stirred for approximately 1 hour. The mixture was added to 30 mL of 30% citric acid solution. The mixture was slowly warmed to ambient temperature and transferred to a separatory funnel. The aqueous phase was separated and extracted with 2×20 mL=40 mL of ethyl acetate. The organic phases were combined, washed with brine, and concentrated to give 11 g crude aldol product as a thick oil. A gas chromatogram showed the oil contained 5.5% of 24, 55% of 22, and 39% of 23.

Example 4

Enzymatic Treatment of a Mixture of 22, 23, and 24 ($R_1$=ethyl, $R_2$=methyl)

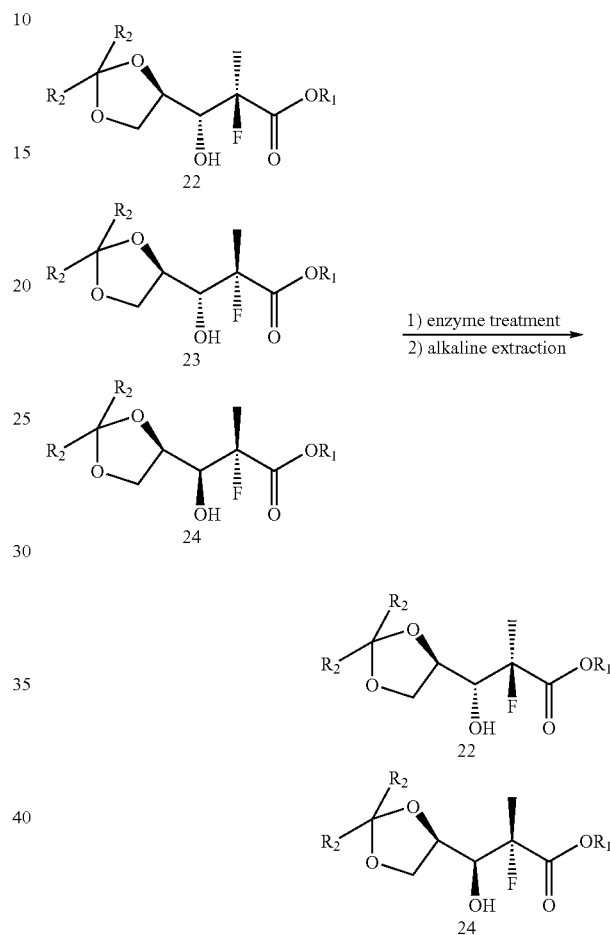

A dry, clean, 1 L, 4-neck round bottom flask, equipped with a mechanic stirrer, a thermo couple, a pH probe, and a base dosing pump inlet, was charged with 360 g of buffer which consisted of 10% D-sorbitol, 3 mM potassium phosphate, and 38.5 g of crude aldol product (22, 23 and 24). The mixture was stirred at 43° C. (batch temperature) and the pH of the mixture was adjusted to ~7.5 by adding 12% $H_2SO_4$ solution. To the mixture was added 4 g of CALB solution. The mixture was stirred at the temperature for 22 hours while the pH was maintained at 7.5 by the addition of 1.0 N NaOH solution via a pH pump. The mixture was cooled to ambient temperature, transferred to a separatory funnel, and extracted with 3×100 mL=300 g of dichloromethane. The organic solution was stirred with 75 g of anhydrous $MgSO_4$ for 1 hour. The solid was filtered and the filtrate was concentrated to dryness to give 18 g crude mixture of 22 and 24 as a thick oil that slowly became a semi-solid.

Example 5

Preparation of 2 (R=Ph) from a Mixture of 22 and 24 (R$_1$=ethyl, R$_2$=methyl)

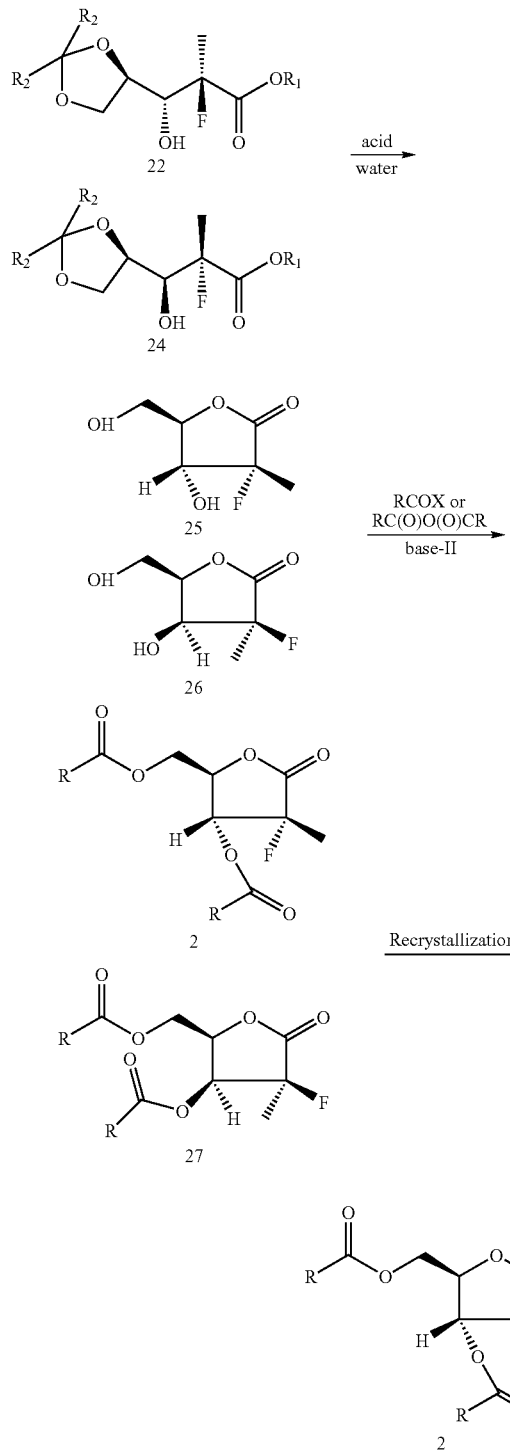

A mixture of 3.0 g of crude mixture of 22 and 24 from Example 4 and 20 g of 2B alcohol and 6 g of 12% sulfuric acid was refluxed at 78° C. for 5 hours. The mixture was cooled to ambient temperature and 1 g of triethylamine was added to neutralize the acid. The mixture was concentrated to dryness. The residue was mixed with 20 g of toluene and the mixture was again concentrated to dryness. The residue was dissolved in 15 g of acetonitrile. To the solution was added a catalytic amount of 4-dimethylaminopyridine (DMAP) and 5.2 g of benzoyl chloride. To this mixture was slowly added 4.1 g of triethylamine while maintaining the batch temperature at <40° C. After the addition the mixture was stirred for 1 hour. The mixture was diluted with 36 g of ethyl acetate and was cooled to 0° C., 25 g of water was added. The mixture was transferred to a separatory funnel and the aqueous phase was separated and extracted again with 20 g of ethyl acetate. The combined organic solution was washed with 20 g of saturated NaHCO$_3$ solution, dried over MgSO$_4$, filtered, and concentrated to give a crude oil. The oil was mixed with 27 g of 2-propanol. The mixture was heated to ~60° C. to become a clear solution. The mixture was then slowly cooled to 10° C. and held for 1 hour. The solid was filtered and the wet cake was washed with 2-propanol and dried under vacuum at 50° C. overnight to give 2.0 g of 2 (R=Ph).

Example 6

Isolation of Pure 22 (R$_1$=ethyl, R$_2$=methyl) after Enzymatic Hydrolysis

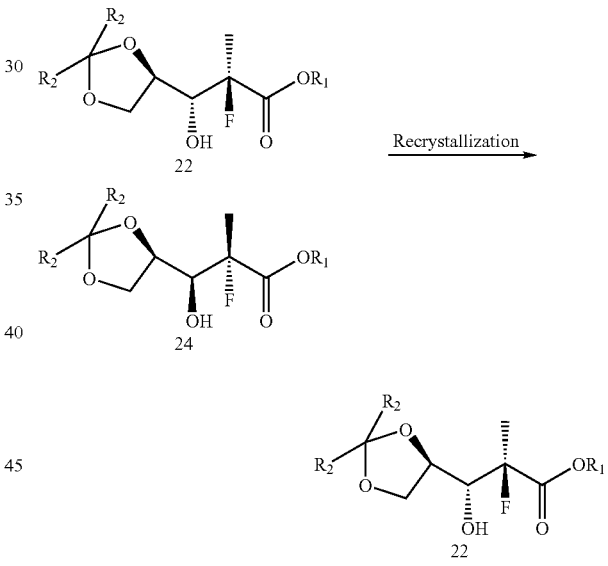

A flask was charged with 3 g of a mixture of 22 and 24 (R$_1$=ethyl, R$_2$=methyl) from Example 4 and 3 ml of tert-butyl methyl ether (TBME). The mixture was stirred until a clear solution was formed. To this solution was slowly added 10 mL of hexanes. The resulted suspension was stirred at ambient temperature for 2 hours. The solid was isolated and washed with 4 mL of hexanes and dried under vacuum at 30° C. overnight to give 1.3 g of pure 22 (R$_1$=ethyl, R$_2$=methyl).

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A method for preparing a mixture of compounds of the formula 22, 23, and 24:

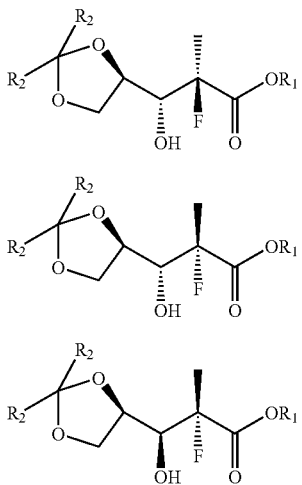

which comprises:
(a) reacting a compound of the formula 20

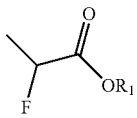

with a non-nucleophilic base-I in a non-reactive solvent; and
(b) reacting the mixture from step (a) with a compound of the formula 21;

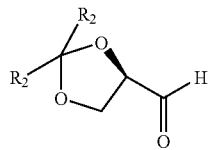

to provide compounds 22, 23, and 24, wherein $R_1$ is a straight chain $C_1$-$C_4$ alkyl group and $R_2$ is selected from the group consisting of methyl, ethyl, n-propyl and n-butyl.

2. The method according to claim 1, wherein $R_1$ is ethyl and $R_2$ is methyl.

3. The method according to claim 1, wherein base-I is selected from the group consisting of lithium diisopropylamide, lithium 2,2,6,6-tetramethylpiperidine, and lithium hexamethyldisilazide.

4. The method according to claim 1, comprising:
(a) mixing anhydrous tetrahydrofuran and diisopropylamine and cooling the mixture to about <–75° C. with stirring;
(b) adding MeLi in ethyl ether to the mixture in step (a) and maintaining the temperature of the mixture at about <–55° C. with stirring;
(c) stirring the mixture in step (b) at about –74° C. for about 30-40 minutes;
(d) adding ethyl 2-fluoropropionate (20, $R_1$=ethyl) to the mixture in step (c) maintaining the temperature of the mixture at about <–74° C. with stirring;
(e) stirring the mixture in step (d) for about 30-50 minutes at about <–76° C.;
(f) adding D-glyceraldehyde, 1,2-acetonide (21, $R_2$=methyl) in anhydrous tetrahydrofuran to the mixture in step (e) maintaining the temperature of the mixture at about <–74° C. with stirring;
(g) stirring the mixture in step (f) for about 20 minutes at about <–74° C.;
(h) adding 20% aqueous ammonium chloride to the mixture in step (g) and allowing the mixture to come to ambient temperature; and
(i) extracting the aqueous phase in step (h) with a volatile organic solvent and evaporating the volatile organic solvent to provide a mixture of compounds of the formula 22, 23, and 24.

5. The method according to claim 1, comprising:
(a) mixing anhydrous tetrahydrofuran and diisopropylamine and cooling the mixture to about <–75° C. with stirring;
(b) adding MeLi in ethyl ether to the mixture in step (a) and maintaining the temperature of the mixture at about <–55° C. with stirring;
(c) stirring the mixture in step (b) at about –74° C. for about 30-40 minutes;
(d) adding ethyl 2-fluoropropionate (20, $R_1$=ethyl) to the mixture in step (c) maintaining the temperature of the mixture at about <–74° C. with stirring;
(e) stirring the mixture in step (d) for about 30-50 minutes at about <–76° C.;
(f) adding D-glyceraldehyde, 1,2-pentanonide (21, $R_2$=ethyl) in anhydrous tetrahydrofuran to the mixture in step (e) maintaining the temperature of the mixture at about <–74° C. with stirring;
(g) stirring the mixture in step (f) for about 20 minutes at about <–74° C.;
(h) adding 20% aqueous ammonium chloride to the mixture in step (g) and allowing the mixture to come to ambient temperature; and
(i) extracting the aqueous phase in step (h) with a volatile organic solvent and evaporating the volatile organic solvent to provide a mixture of compounds of the formula 22, 23, and 24.

6. The method according to claim 1, comprising:
(a) mixing anhydrous toluene and diisopropylamine and cooling the mixture to about <–75° C. with stirring;
(b) adding MeLi in ethyl ether to the mixture in step (a) and maintaining the temperature of the mixture at about <–55° C. with stirring;
(c) stirring the mixture in step (b) at about –74° C. for about 30-40 minutes;
(d) adding n-butyl 2-fluoropropionate (20, $R_1$=n-butyl) to the mixture in step (c) maintaining the temperature of the mixture at about <–70° C. with stirring;
(e) stirring the mixture in step (d) for about 30-50 minutes at about <–76° C.;
(f) adding D-glyceraldehyde, 1,2-acetonide (21, $R_2$=methyl) in anhydrous toluene to the mixture in step (e) maintaining the temperature of the mixture at about <–74° C. with stirring;
(g) stirring the mixture in step (f) for about 20 minutes at about <–74° C.;
(h) adding 30% citric acid to the mixture in step (g) and allowing the mixture to come to ambient temperature; and
(i) extracting the aqueous phase in step (h) with a volatile organic solvent and evaporating the volatile organic solvent to provide a mixture of compounds of the formula 22, 23, and 24.

7. A method for preparing a mixture of compounds of the formula 22 and 24:

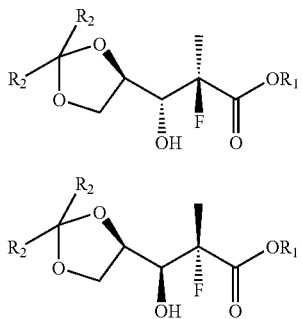

22

24 which comprises:
(a) reacting a mixture of compounds of the formula 22, 23, and 24:

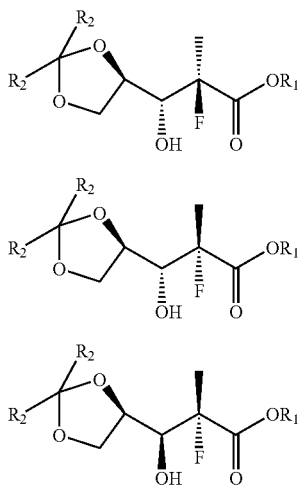

22

23

24 with an enzyme which preferentially hydrolyzes compound 23 to the corresponding carboxylic acid in an alkaline aqueous medium; and
(b) extracting the alkaline aqueous medium from step (a) with a volatile organic solvent to provide compounds 22 and 24;

wherein $R_1$ is a straight chain $C_1$-$C_4$ alkyl group and $R_2$ is selected from the group consisting of methyl, ethyl, n-propyl and n-butyl.

8. The method according to claim 7, wherein $R_1$ is ethyl and $R_2$ is methyl.

9. The method according to claim 7, wherein the enzyme in step (b) is Candida Antarctica Lipase 2 (CALB).

10. The method according to claim 7, comprising:
(a) mixing 3 mM of potassium phosphate buffer containing 10% aqueous D-sorbitol and a mixture of compounds of the formula 22, 23, and 24 ($R_1$=ethyl, $R_2$=methyl);
(b) stirring the mixture in step (a) within a temperature range of about 20-45° C.;
(c) adding Candida Antarctica lipase form B to the mixture in step (b), maintaining the pH at about 7.0-7.5, and stirring the mixture until the compound of the formula 23 is hydrolyzed;
(d) allowing the mixture in step (c) to come to ambient temperature; and (e) extracting the aqueous phase in step (d) with a volatile organic solvent and evaporating the volatile organic solvent to provide a mixture of compounds of the formula 22 and 24.

11. A method for preparing a compound of the formula 2:

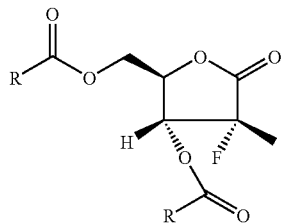

2 which comprises:
(a) acidically hydrolyzing a mixture of compounds of the formula 22 and 24:

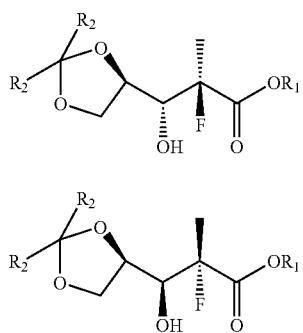

22

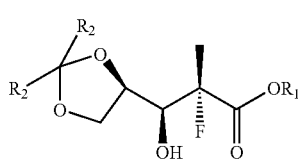

24 to form a mixture of compounds of the formula 25 and 26:

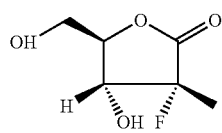

25

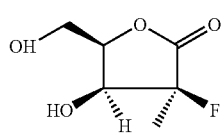

26

(b) acylating compounds 25 and 26 from step (a) with an acyl halide, RCOX, or an acyl anhydride, RC(O)O(O)CR, in the presence of a non-nucleophilic base-II, which does not react with acyl halides, in a non-reactive solvent to form compounds of the formula 2 and 27; and

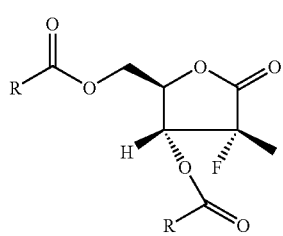

2

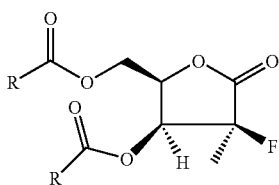

(c) recrystallizing the mixture of compounds 2 and 27 from step (b) from an aqueous-soluble organic solvent capable of providing crystalline compound 2;

wherein R is a straight or branched $C_1$-$C_6$ alkyl group or is an arylalkyl group substituted with one or two $C_1$-$C_3$ alkyl groups; $R_1$ is a straight chain $C_1$-$C_4$ alkyl group; $R_2$ is selected from the group consisting of methyl, ethyl, n-propyl and n-butyl; and X is halogen.

12. The method according to claim 11, wherein R is phenyl, $R_1$ is ethyl, $R_2$ is methyl, and X is chloro.

13. The method according to claim 11, wherein the acidic hydrolyzing in step (a) is carried out with an acid selected from the group consisting of acetic acid, sulfuric acid, hydrochloric acid, methanesulfonic acid, and trifluoroacetic acid.

14. The method according to claim 11, wherein the base-II in step (b) is a tertiary amine.

15. The method according to claim 14, wherein base-II is selected from the group consisting of pyridine, triethylamine, and N,N'-diisopropylethylamine.

16. The method according to claim 11, wherein the aqueous-soluble organic solvent capable of providing crystalline compound 2 in step (c) is selected from the group consisting of methanol, ethanol, n-propanol, and isopropanol.

17. The method according to claim 16, wherein the solvent is isopropanol.

18. The method according to claim 11, comprising:
(a) heating to reflux a mixture of compounds of the formula 22 and 24 ($R_1$=ethyl, $R_2$=methyl) in ethanol with 12% sulfuric acid for about 5 hours;
(b) cooling the mixture in step (a) to ambient temperature and adding triethylamine to neutralize the mixture;
(c) concentrating the mixture in step (b) to dryness and adding toluene to the mixture and again concentrating the mixture to dryness;
(d) dissolving the mixture in step (c) in acetonitrile and adding benzoyl chloride and a catalytic amount of 4-dimethylaminopyridine;
(e) adding triethylamine to the mixture in step (d) while maintaining the mixture temperature at about <40° C. for about an hour;
(f) adding ethyl acetate to the mixture in step (e) and cooling the mixture to about 0° C. and then adding water;
(g) separating the ethyl acetate phase in step (f) and evaporating the ethyl acetate; and
(h) adding 2-propanol to the mixture in step (g), heating the mixture to about 60° C. to obtain a clear solution, and then cooling the solution to about 10° C. to precipitate a compound of the formula 2.

19. A method for preparing a compound of the formula 22:

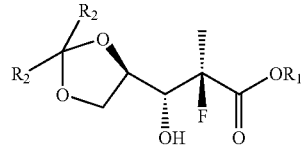

which comprises:
(a) providing a mixture of compounds of the formula 22 and 24:

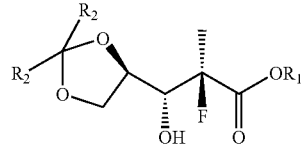

(b) recrystallizing the mixture of compounds 22 and 24 from step (a) from a volatile organic solvent to provide compound 22;

wherein $R_1$ is a straight chain $C_1$-$C_4$ alkyl group and $R_2$ is selected from the group consisting of methyl, ethyl, n-propyl and n-butyl.

20. The method according to claim 19, wherein $R_1$ is ethyl and $R_2$ is methyl.

21. The method according to claim 19, wherein the solvent is a $C_5$-$C_8$ hydrocarbon solvent.

22. The method according to claim 21, wherein the solvent is hexane.

23. The method according to claim 19, further comprising dissolving compounds 22 and 24 in tert-butyl methyl ether and then adding hexane.

24. The method according to claim 19, comprising:
(a) stirring a mixture of compounds of the formula 22 and 24 ($R_1$=ethyl, $R_2$=methyl) in tert-butyl methyl ether to form a clear solution;
(b) adding hexane to the mixture in step (a) to form a suspension and stirring the suspension at ambient temperature for about 2 hours; and
(c) separating the solid from the suspension in step (b) to provide compound 22.

* * * * *